(12) United States Patent
Eicken et al.

(10) Patent No.: US 6,509,501 B2
(45) Date of Patent: Jan. 21, 2003

(54) BENZAMIDOXIME DERIVATIVES, INTERMEDIATES AND PROCESSES FOR THEIR PREPARATION, AND THEIR USE AS FUNGICIDES

(75) Inventors: Karl Eicken, Wachenheim (DE); Joachim Rheinheimer, Ludwigshafen (DE); Frank Wetterich, Mutterstadt (DE); Eberhard Ammermann, Heppenheim (DE); Gisela Lorenz, Neustadt (DE); Siegfried Strathmann, Limburgerhof (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/093,634
(22) Filed: Mar. 11, 2002

(65) Prior Publication Data
US 2002/0133025 A1 Sep. 19, 2002

Related U.S. Application Data

(62) Division of application No. 09/508,597, filed as application No. PCT/EP98/05617 on Sep. 5, 1998, now Pat. No. 6,417,398.

(30) Foreign Application Priority Data

| Sep. 18, 1997 | (DE) | 19741099 |
| Dec. 3, 1997 | (DE) | 19753519 |
| Jan. 23, 1998 | (DE) | 19802459 |

(51) Int. Cl.$^7$ .......................... C07C 251/48
(52) U.S. Cl. ........................ 564/265; 564/229
(58) Field of Search ................. 564/229, 265

(56) References Cited

U.S. PATENT DOCUMENTS

| 5,185,027 A | 2/1993 | Vogelbacher |
| 5,362,876 A | 11/1994 | Eicken |

FOREIGN PATENT DOCUMENTS

| CA | 2123242 | 11/1994 |
| EP | 353 631 | 2/1990 |
| JP | 9-235262 | 9/1997 |

OTHER PUBLICATIONS

JP 02006453 Abstracts of Japan, Hiroyasu, 1990.
JP 09235262 Abstracts of Japan, Homare, 1997.
JP 01034954 Abstracts of Japan, Takuo, 1989.
JP 01215994 Abstracts of Japan, Ten, 1989.

Primary Examiner—Shailendra Kumar
(74) Attorney, Agent, or Firm—Keil & Weinkauf

(57) ABSTRACT

Benzamidoxime derivatives of the formula I

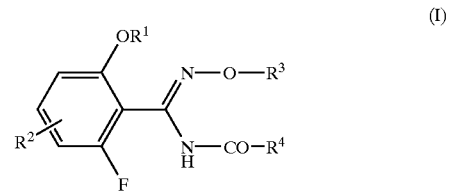

where
- $R^1$ is difluoromethyl or trifluoromethyl
- $R^2$ is hydrogen or fluorine
- $R^3$ is $C_1$–$C_4$-alkyl which may be substituted by cyano, $C_1$–$C_4$-haloalkyl, $C_1$–$C_4$-alkoxy-$C_1$–$C_4$-alkyl, $C_3$–$C_6$-alkenyl, $C_3$–$C_6$-haloalkenyl, $C_3$–$C_6$-alkynyl, $C_3$–$C_8$-cycloalkyl-$C_1$–$C_4$-alkyl
- $R^4$ is phenyl-$C_1$–$C_6$-alkyl which may carry one or more substitutents selected from the group consisting of halogen, $C_1$–$C_4$-alkyl, $C_1$–$C_4$-haloalkyl, $C_1$–$C_4$-alkoxy and $C_1$–$C_4$-haloalkoxy on the phenyl ring, or
- is thienyl-$C_1$–$C_4$-alkyl which may carry one or more substituents selected from the group consisting of halogen, $C_1$–$C_4$-alkyl, $C_1$–$C_4$-haloalkyl, $C_1$–$C_4$-alkoxy and $C_1$–$C_4$-haloalkoxy on the thienyl ring, or
- is pyrazolyl-$C_1$–$C_4$-alkyl which may carry one or more substituents selected from the group consisting of halogen, $C_1$–$C_4$-alkyl, $C_1$–$C_4$-haloalkyl, $C_1$–$C_4$-alkoxy and $C_1$–$C_4$-haloalkoxy on the pyrazole ring, are prepared, and intermediates for their preparation and their use as fungicides are described.

4 Claims, No Drawings

BENZAMIDOXIME DERIVATIVES, INTERMEDIATES AND PROCESSES FOR THEIR PREPARATION, AND THEIR USE AS FUNGICIDES

This is a Divisional application of application Ser. No. 09/508,597, filed on Mar. 14, 2000 now U.S. Pat. No. 6,417,398; which is a 317 of PCT/EP98/05617, filed Sep. 5, 1998.

The present invention relates to novel benzamidoxime derivatives, to processes and intermediates for their preparation and to their use as fungicides.

JP-A 02/006453 describes fungicidally active benzamidoxime derivatives which, however, are not entirely satisfactory, in particular when low rates of application are used.

It is an object of the present invention to provide novel benzamidoxime derivatives which have improved activity, in particular even at low rates of application.

We have found that this object is achieved by benzamidoxime derivatives of the formula I

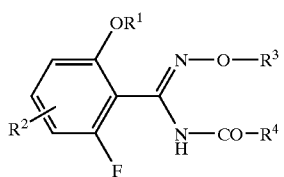

where:
R$^1$ is difluoromethyl or trifluoromethyl
R$^2$ is hydrogen or fluorine
R$^3$ is $C_1$–$C_4$-alkyl which may be substituted by cyano, $C_1$–$C_4$-haloalkyl, $C_1$–$C_4$-alkoxy-$C_1$–$C_4$-alkyl, $C_3$–$C_6$-alkenyl, $C_3$–$C_6$-haloalkenyl, $C_3$–$C_6$-alkynyl, $C_3$–$C_8$-cycloalkyl-$C_1$–$C_4$-alkyl
R$^4$ is phenyl-$C_1$–$C_6$-alkyl which may carry one or more substitutents selected from the group consisting of halogen, $C_1$–$C_4$-alkyl, $C_1$–$C_4$-haloalkyl, $C_1$–$C_4$-alkoxy and $C_1$–$C_4$-haloalkoxy on the phenyl ring, or is thienyl-$C_1$–$C_4$-alkyl which may carry one or more substituents selected from the group consisting of halogen, $C_1$–$C_4$-alkyl, $C_1$–$C_4$-haloalkyl, $C_1$–$C_4$-alkoxy and $C_1$–$C_4$-haloalkoxy on the thienyl ring, or is pyrazolyl-$C_1$–$C_4$-alkyl which may carry one or more substituents selected from the group consisting of halogen, $C_1$–$C_4$-alkyl, $C_1$–$C_4$-haloalkyl, $C_1$–$C_4$-alkoxy and $C_1$–$C_4$-haloalkoxy on the pyrazole ring.

In the definition of the substituents R$^1$ to R$^4$, the terms indicated are a collective term for a group of compounds.

Halogen is in each case fluorine, bromine, chlorine or iodine, in particular fluorine or chlorine.

Other meanings are, for example:

$C_1$–$C_4$-alkyl: methyl, ethyl, n-propyl, 1-methylethyl, n-butyl, 1-methylpropyl, 2-methylpropyl or 1,1-dimethylethyl, in particular ethyl;

$C_1$–$C_4$-haloalkyl: a $C_1$–$C_4$-alkyl radical as mentioned above which is partially or fully substituted by fluorine, chlorine, bromine and/or iodine, for example trichloromethyl, trifluoromethyl, 2-fluoroethyl, 2-chloroethyl, 2-bromoethyl, 2,2-difluoroethyl, 2,2,2-trifluoroethyl, 2,2,2-trichloroethyl, 2-fluoropropyl, 3-fluoropropyl, 2-chloropropyl or 3-chloropropyl, in particular 2-fluoroethyl or 2-chloroethyl;

cyano-$C_1$–$C_4$-alkyl: for example cyanomethyl, 1-cyanoeth-1-yl, 2-cyanoeth-1-yl, 1-cyanoprop-1-yl, 2-cyanoprop-1-yl, 3-cyanoprop-1-yl, 1-cyanoprop-2-yl or 2-cyanoprop-2-yl, in particular cyanomethyl or 2-cyanoethyl;

$C_1$–$C_4$-alkoxy: methoxy, ethoxy, n-propoxy, 1-methylethoxy, n-butoxy, 1-methylpropoxy, 2-methylpropoxy or 1,1-dimethylethoxy, in particular methoxy or ethoxy;

$C_1$–$C_4$-alkoxy-$C_1$–$C_4$-alkyl: $C_1$–$C_4$-alkyl which is substituted by $C_1$–$C_4$-alkoxy as mentioned above, i.e. for example methoxymethyl, ethoxymethyl, n-propoxymethyl, (1-methylethoxy)methyl, n-butoxymethyl, (1-methylpropoxy)methyl, (2-methylpropoxy)methyl, (1,1-dimethylethoxy)methyl, 2-(methoxy)ethyl or 2-(ethoxy)ethyl, in particular methoxymethyl or 2-methoxyethyl;

$C_3$–$C_6$-alkenyl: for example prop-2-en-1-yl, n-buten-4-yl, 1-methylprop-2-en-1-yl, 2-methylprop-2-en-1-yl or 2-buten-1-yl, in particular prop-2-en-1-yl;

$C_3$–$C_6$-haloalkenyl: $C_3$–$C_6$-alkenyl as mentioned above which is partially or fully substituted by fluorine, chlorine and/or bromine, for example 2-chloroallyl, 3-chloroallyl, 2,3-dichloroallyl or 3,3-dichloroallyl, in particular 2-chloroallyl;

$C_3$–$C_6$-alkynyl: for example prop-1-yn-1-yl, prop-2-yn-1-yl, n-but-1-yn-1-yl, n-but-1-yn-3-yl, n-but-1-yn-4-yl or n-but-2-yn-1-yl, in particular prop-2-yn-1-yl;

$C_3$–$C_8$-cycloalkyl-$C_1$–$C_4$-alkyl: for example cyclopropylmethyl, cyclobutylmethyl, cyclopentylmethyl, cyclohexylmethyl, (cyclopropyl)ethyl, 1-(cyclobutyl)ethyl, 1-(cyclopentyl)ethyl, 1-(cyclohexyl)ethyl, 1-(cycloheptyl)ethyl, 1-(cyclooctyl)ethyl, 2-(cyclopropyl)ethyl or 2-(cyclobutyl)ethyl, in particular cyclopentylmethyl;

phenyl-$C_1$–$C_6$-alkyl: for example benzyl, 1-phenylethyl, 2-phenylethyl, 1-phenylprop-1-yl, 2-phenylprop-1-yl, 3-phenylprop-1-yl, in particular benzyl or 2-phenylethyl;

thienyl-$C_1$–$C_4$-alkyl: for example 2-thienylmethyl, 3-thienylmethyl or 2-thienylethyl;

pyrazolyl-$C_1$–$C_4$-alkyl: for example 1-pyrazolylmethyl, 2-pyra-zolylmethyl, 3-pyrazolylmethyl or 2-pyrazolylethyl.

Compounds in which the substituent R$^1$ is difluoromethyl, the substituent R$^3$ is cyclopropylmethyl and the substituent R$^4$ is benzyl which carries one to three substituents selected from the group mentioned above on the phenyl ring, in particular one to three substituents selected from the group consisting of fluorine, chlorine, methyl, methoxy or trifluoromethyl, have generally proved especially effective.

Compounds of the formula I where R$^1$ to R$^4$ have the meanings listed in Table 1 below are particularly preferred.

TABLE 1

| No. | R¹ | R² | R³ | R⁴ | M.p. ° C. |
|---|---|---|---|---|---|
| I.1 | $CHF_2$ | H | $C_2H_5$ | $C_6H_5-CH_2$ | oil |
| I.2 | $CHF_2$ | H | $C_2H_5$ | $4-CH_3O-C_6H_4-CH_2$ | oil |
| I.3 | $CHF_2$ | H | $CH_2-CH=CH_2$ | $C_6H_5-CH_2$ | oil |
| I.4 | $CHF_2$ | H | $CH_2-C\equiv CH$ | $C_6H_5-CH_2$ | oil |
| I.1 | $CHF_2$ | H | $C_2H_5$ | $C_6H_5-CH_2$ | oil |
| I.2 | $CHF_2$ | H | $C_2H_5$ | $4-CH_3O-C_6H_4-CH_2$ | oil |
| I.3 | $CHF_2$ | H | $CH_2-CH=CH_2$ | $C_6H_5-CH_2$ | oil |
| I.4 | $CHF_2$ | H | $CH_2-C\equiv CH$ | $C_6H_5-CH_2$ | oil |
| I.5 | $CHF_2$ | H | $CH_2-C\equiv CH$ | $4-CH_3O-C_6H_4-CH_2$ | oil |
| I.6 | $CHF_2$ | H | cPr | $C_6H_5-CH_2$ | |
| I.7 | $CF_3$ | H | cPr | $C_6H_5-CH_2$ | |
| I.8 | $CHF_2$ | H | cPr | $4-F-C_6H_4-CH_2$ | 75–77 |
| I.9 | $CHF_2$ | H | cPr | $4-Cl-C_6H_4-CH_2$ | 81–83 |
| I.10 | $CHF_2$ | H | cPr | $4-CH_3O-C_6H_4-CH_2$ | 57–59 |
| I.11 | $CHF_2$ | H | cPr | $4-CF_3C_6H_4-CH_2$ | |
| I.12 | $CHF_2$ | H | cPr | 2-Thienylmethyl | oil |
| I.13 | $CHF_2$ | H | cPr | 3-Thienylmethyl | oil |
| I.14 | $CHF_2$ | H | cPr | Pyrazolyl-1-methyl | |
| I.15 | $CHF_2$ | H | cPr | $4-CH_3-C_6H_4-CH_2$ | |
| I.16 | $CHF_2$ | 5-F | $CH_2-CH=CH_2$ | $C_6H_5-CH_2$ | |
| I.17 | $CHF_2$ | 5-F | $CH_2-CH=CH_2$ | $4-CH_3-C_6H_4-CH_2$ | |
| I.18 | $CHF_2$ | 5-F | $CH_2-C\equiv CH$ | $C_6H_5-CH_2$ | |
| I.19 | $CHF_2$ | 5-F | $CH_2-C\equiv CH$ | $4-CH_3O-C_6H_4CH_2$ | |
| I.20 | $CHF_2$ | 5-F | cPr | $C_6H_5-CH_2$ | 62–65 |
| I.21 | $CHF_2$ | 5-F | cPr | $4-F-C_6H_4-CH_2$ | 64–67 |
| I.22 | $CHF_2$ | 5-F | cPr | $4-Cl-C_6H_4-CH_2$ | 72–75 |
| I.23 | $CHF_2$ | 5-F | cPr | $4-CH_3-C_6H_4-CH_2$ | 74–76 |
| I.24 | $CHF_2$ | 5-F | cPr | $4-CH_3-C_6H_4-CH_2$ | 79–81 |
| I.25 | $CHF_2$ | 5-F | cPr | $4-CF_3-C_6H_4-CH_2$ | |
| I.26 | $CF_3$ | 5-F | cPr | $C_6H_5-CH_2$ | |
| I.27 | $CHF_2$ | 4-F | cPr | $C_6H_5-CH_2$ | |
| I-28 | $CHF_2$ | 4-F | cPr | $4-CH_3O-C_6H_4-CH_2$ | |
| I.29 | $CHF_2$ | H | cPr | $4-CH_3C_6H_4-CH_2$ | 69–71 |
| I.30 | $CHF_2$ | H | $CH_2-C\equiv CH$ | $4-F-C_6H_4-CH_2$ | 74–76 |
| I.31 | $CHF_2$ | H | $C_2H_5$ | $4-F-C_6H_4-CH_2$ | oil |
| I.32 | $CHF_2$ | H | $CH_2-CH=CH_2$ | $4-F-C_6H_4-CH_2$ | oil |
| I.33 | $CHF_2$ | H | $CH_2-CH=CH_2$ | $4-CH_3O-C_6H_4-CH_2$ | oil |
| I.34 | $CHF_2$ | H | $CH_2-CH(CH_3)_2$ | $C_6H_5-CH_2$ | 65–67 |
| I.35 | $CHF_2$ | H | $CH_2-C(CH_3)=CH_2$ | $C_6H_5-CH_2$ | oil |

In the above table, cPr is cyclopropylmethyl

The benzamidoxime derivatives according to the invention of the formula I are obtained by the process according to the invention by means of ether cleavage of fluorinated benzonitriles of the formula II, reaction of the resulting benzonitriles III with haloalkanes $CH_mF_nHal$ (m has the value 0 or 1, n the value 2 or 3), such as $CHF_2Cl$ or $CF_3I$, in an alkaline medium (preferably in the presence of an alkali metal hydroxide) to give benzonitriles IV and subsequent reaction of IV with hydroxylamine or salts thereof in aqueous solution, preferably in water or water/alkanol mixtures, in the presence or absence of a base, to give the benzamidoximes of the formula V, which are then subsequently alkylated in a manner known per se to give the precursors VI.

The benzamidoximes VI can then be acylated in a manner known per se with the suitable acyl halides, preferably the suitable acyl chlorides, by heating in inert solvents (preferably at from 20 to 100° C.).

Particularly suitable inert solvents are hydrocarbons or ethers, especially preferably aromatic hydrocarbons, such as toluene or xylene, to mention but two examples.

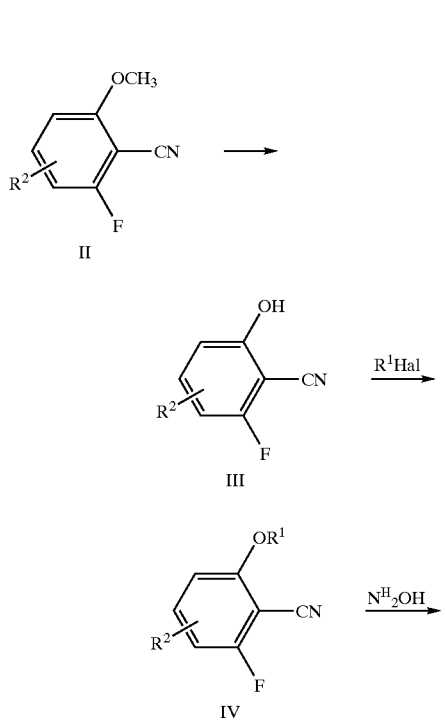

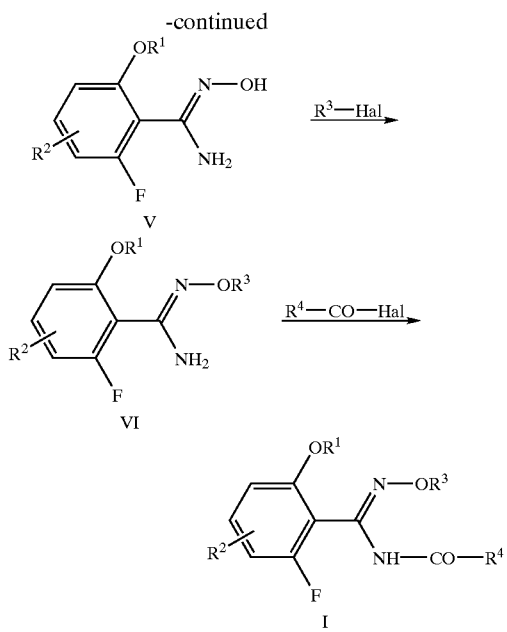

$R^1$ in the above equation is a group $CH_mF_n$, where m is 0 or 1 and n is 2 or 3.

The intermediates of the formula III where $R^2$ is fluorine and the intermediates of the formulae IV, V and VI, all of which are given in the above equation, are novel and also form part of the subject matter of the invention.

Starting from 2,3-difluoro-6-methoxybenzaldehyde (which can be prepared, for example, by the process of Example 27 of WO 97/03071), the preparation of these novel intermediates having a difluoro substitution can be carried through to the stage of the compounds IV using the variants described in Example 2. The further steps in the preparation of the corresponding compounds V and VI are known per se to the person skilled in the art.

Preferred compounds of the formulae IV, V and VI are those where $R^2$ and $R^3$ (compounds VI) have the meanings given above for compounds of the formula I.

Preferred compounds of the formula IV are the compounds given in Table 2 below (m and n have the abovementioned meanings).

| No. | $R^2$ | m | n | M.p.[° C.], NMR (CDCl$_3$) ppm |
|---|---|---|---|---|
| II.1 | H | 1 | 2 | 6.7 t(1 H);7.05–7.2 m(2 H);7.55–7.7 m(1 H) |
| II.2 | 5-F | 1 | 2 | 6.65 t(1 H);7.05–7.2 m(1 H);7.4–7.5 m(1 H) |
| II.3 | 4-F | 1 | 2 | |
| II.4 | H | 0 | 3 | |
| II.5 | 5-F | 0 | 3 | |

Preferred compounds of the formula V are given in Table 3.

| No. | $R^2$ | m | n | M.p.[° C.], NMR (CDCl$_3$) ppm |
|---|---|---|---|---|
| III.1 | H | 1 | 2 | 5.9 s(2 H);7.0–7.2 m(2 H);7.15 t(1 H);7.4–7.55 m (1 H) |
| III.2 | 5-F | 1 | 2 | 4.9 s(2 H);6.5 t(1 H); 6.95–7.05 m(1 H); 7.15–7.3 m(1 H); 8.0 s(1 H) |
| III.3 | 4-F | 1 | 2 | |
| III.4 | H | 0 | 3 | |
| III.5 | 5-F | 0 | 3 | |

Some preferred compounds of the formula VI are given in Table 4 below.

| No. | $R^2$ | $R^3$ | m | n | M.p. [° C.], NMR (CDCl$_3$) ppm |
|---|---|---|---|---|---|
| IV.1 | H | $C_2H_5$ | 1 | 2 | |
| IV.2 | H | $CH_2$—CH=$CH_2$ | 1 | 2 | |
| IV.3 | H | $CH_2$—C≡CH | 1 | 2 | |
| IV.4 | H | c-Pr | 1 | 2 | 0.3 m(2 H);0.55 m(2 H);1.2 m(2 H);3.9 d(2 H);4.85 s, brd(2 H);6.6 t(1 H); 6.85–7.1 m(2 H) 7.35–7.45 m(1 H) |
| IV.5 | H | $CH_2$—C≡CH | 0 | 3 | |
| IV.6 | H | c-Pr | 0 | 3 | |
| IV.7 | 5-F | $C_2H_5$ | 1 | 2 | |
| IV.8 | 5-F | $CH_2$—CH=$CH_2$ | 1 | 2 | |
| IV.9 | 5-F | $CH_2$—C≡CH | 1 | 2 | |
| IV.10 | 5-F | c-Pr | 1 | 2 | 0.3 m(2 H); 0.55 m(2 H); 1.2 m(1 H);3.85 d(2 H); 4.9 s brd(2 H);6.55 t(1 H); 7.0–7.1 m(1 H); 7.15–7.2 m(1 H) |

The compounds I are distinguished by an outstanding activity against a broad spectrum of phytopathogenic fungi, in particular from the classes of the Ascomycetes, Deuteromycetes, Phycomycetes and Basidiomycetes. Some of them act systemically, and they can therefore also be employed as foliar- and soil-acting fungicides.

Normally, the plants are sprayed or dusted with the active ingredients, or the seeds of the plants are treated with the active ingredients.

The formulations are prepared in a known manner, e.g. by extending the active ingredient with solvents and/or carriers, if desired using emulsifiers and dispersants, it also being possible to use other organic solvents as auxiliary solvents if water is used as the diluent. Auxiliaries which are suitable are essentially: solvents such as aromatics (e.g. xylene), chlorinated aromatics (e.g. chlorobenzenes), paraffins (e.g. mineral oil fractions), alcohols (e.g. methanol, butanol), ketones (e.g. cyclohexanone), amines (e.g. ethanolamine, dimethylformamide) and water; carriers such as ground natural minerals (e.g. kaolins, clays, talc, chalk) and ground synthetic minerals (e.g. highly disperse silica, silicates); emulsifiers such as nonionic and anionic emulsifiers (e.g. polyoxyethylene fatty alcohol ethers, alkylsulfonates and arylsulfonates) and dispersants such as lignin-sulfite waste liquors and methylcellulose.

Suitable surfactants are the alkali metal salts, alkaline earth metal salts and ammonium salts of aromatic sulfonic acids, e.g. ligno-, phenol-, naphthalene- and dibutylnaphthalenesulfonic acid, and of fatty acids, alkylsulfonates, alkylarylsulfonates, alkyl sulfates, lauryl ether sulfates and fatty alcohol sulfates, and salts of sulfated hexa-, hepta- and octadecanols, and of fatty alcohol glycol ethers, condensates of sulfonated naphthalene and its derivatives with formaldehyde, condensates of naphthalene or of the naphthalenesulfonic acids with phenol or formaldehyde, polyoxyethylene octylphenol ether, ethoxylated iso-octylphenol, octylphenol or nonylphenol, alkylphenyl polyglycol ether, tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene, lauryl alcohol polyglycol ether acetate, sorbitol esters, lignin-sulfite waste liquors and methylcellulose.

Powders, materials for spreading and dusts can be prepared by mixing or concomitantly grinding the active substances with a solid carrier.

Granules, e.g. coated granules, impregnated granules and homogeneous granules, can be prepared by binding the active ingredients to solid carriers. Solid carriers are mineral earths, such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers, such as ammonium sulfate, ammonium phosphate, ammonium nitrate, ureas, and products of vegetable origin, such as cereal meal, tree bark meal, wood meal and nutshell meal, cellulose powders or other solid carriers.

The following are examples of such formulations:

I. a solution, suitable for use in the form of microdrops, of 90 parts by weight of a compound I according to the invention and 10 parts by weight of N-methyl-2-pyrrolidone;

II. a mixture of 10 parts by weight of a compound I according to the invention, 70 parts by weight of xylene, 10 parts by weight of the adduct of 8 to 10 mol of ethylene oxide and 1 mol of oleic acid N-monoethanolamide, 5 parts by weight of calcium dodecylbenzenesulfonate, 5 parts by weight of the adduct of 40 mol of ethylene oxide and 1 mol of castor oil; a dispersion is obtained by finely distributing the solution in water.

III. an aqueous dispersion of 10 parts by weight of a compound I according to the invention, 40 parts by weight of cyclohexanone, 30 parts by weight of isobutanol, 20 parts by weight of the adduct of 40 mol of ethylene oxide and 1 mol of castor oil;

IV. an aqueous dispersion of 10 parts by weight of a compound I according to the invention, 25 parts by weight of cyclohexanol, 55 parts by weight of a mineral oil fraction of boiling point 210 to 280° C. and 10 parts by weight of the adduct of 40 mol of ethylene oxide and 1 mol of castor oil;

V. a mixture, ground in a hammer mill, of 80 parts by weight, preferably of a solid compound I according to the invention, 3 parts by weight of sodium di-isobutylnaphthalene-2-sulfonate, 10 parts by weight of the sodium salt of a lignosulfonic acid from a sulfite waste liquor and 7 parts by weight of pulverulent silica gel; a spray mixture is obtained by finely distributing the mixture in water;

VI. an intimate mixture of 3 parts by weight of a compound I according to the invention and 97 parts by weight of finely divided kaolin; this dust comprises 3% by weight of active ingredient;

VII. an intimate mixture of 30 parts by weight of a compound I according to the invention, 62 parts by weight of pulverulent silica gel and 8 parts by weight of paraffin oil which had been sprayed onto the surface of this silica gel; this formulation imparts good adhesion to the active ingredient;

VIII. a stable aqueous dispersion of 40 parts by weight of a compound I according to the invention, 10 parts by weight of the sodium salt of a phenolsulfonic acid/urea/formaldehyde condensate, 2 parts by weight of silica gel and 48 parts by weight of water; this dispersion can be diluted further;

IX. a stable oily dispersion of 20 parts by weight of a compound I according to the invention, 2 parts by weight of calcium dodecylbenzenesulfonate, 8 parts by weight of fatty alcohol polyglycol ether, 20 parts by weight of the sodium salt of a phenolsulfonic acid/urea/formaldehyde condensate and 50 parts by weight of a paraffinic mineral oil.

The novel compounds are distinguished by an outstanding activity against a broad spectrum of phytopathogenic fungi, in particular from the classes of the Deuteromycetes, Ascomycetes, Phycomycetes and Basidiomycetes. Some of them act systemically, and they can be employed as foliar- and soil-acting fungicides.

They are especially important for controlling a large number of fungi on a variety of crop plants such as wheat, rye, barley, oats, rice, maize, turf, cotton, soya, coffee, sugar cane, grapevines, fruit species, ornamentals and vegetables such as cucumbers, beans and cucurbits, and on the seeds of these plants.

The compounds are applied by treating the fungi, or the seeds, plants, materials or the soil to be protected against fungal infection, with a fungicidally effective amount of the active ingredients.

Application is effected before or after infection of the materials, plants or seeds by the fungi.

Specifically, the novel compounds are suitable for controlling the following plant diseases:

*Erysiphe graminis* (powdery mildew) in cereals, *Erysiphe cichoracearum* and *Sphaerotheca fuliginea* on cucurbits, *Podosphaera leucotricha* on apples, *Uncinula necator* on grapevines, Puccinia species on cereals, Rhizoctonia species on cotton and turf, Ustilago species on cereals and sugar cane, *Venturia inaequalis* (scab) on apples, Helminthosporium species on cereals, *Septoria nodorum* on wheat, *Botrytis cinerea* (gray mold) on strawberries, grapevines, ornamentals and vegetables, *Cercospora arachidicola* on peanuts, *Pseudocercosporella herpotrichoides* on wheat, barley, *Pyricularia oryzae* on rice, *Phytophthora infestans* on potatoes and tomatoes, Fusarium and Verticillium species on a variety of plants, *Plasmopara viticola* on grapevines and Alternaria species on vegetables and fruit.

The novel compounds can also be employed in the protection of materials (protection of wood), for example against Paecilomyces variotii.

In general, the fungicidal compositions comprise from 0.1 to 95, preferably from 0.5 to 90, % by weight of active ingredient.

Depending on the nature of the desired effect, the rates of application are from 0.025 to 2, preferably 0.1 to 1, kg of active ingredient per ha.

In the treatment of seed, amounts of 0.001 to 50, preferably 0.01 to 10, g of active ingredient are generally required per kilogram of seed.

In the use form as fungicides, the agents according to the invention can also be present together with other active ingredients, e.g. with herbicides, insecticides, growth regulators, fungicides or else with fertilizers.

A mixture with fungicides frequently results in a broader fungicidal spectrum of action.

The following list of fungicides together with which the compounds according to the invention can be applied is intended to illustrate the possible combinations, but not to impose any limitation:

sulfur, dithiocarbamates and their derivatives, such as iron(III) dimethyldithiocarbamate, zinc dimethyldithiocarbamate, zinc ethylenebisdithiocarbamate, manganese ethylenebisdithiocarbamate, manganese zinc ethylenediaminebisdithiocarbamate, tetramethylthiuram disulfide, ammonia complex of zinc (N,N-ethylenebisdithiocarbamate), ammonia complex of zinc (N,N'-propylenebisdithiocarbamate), zinc (N,N'-propylenebisdithiocarbamate), N,N'-polypropylenebis (thiocarbamoyl)disulfide;

nitro derivatives, such as dinitro-(1-methylheptyl)phenyl crotonate, 2-sec-butyl-4,6-dinitrophenyl 3,3-dimethylacrylate, 2-sec-butyl-4,6-dinitrophenylisopropyl carbonate, diisopropyl 5-nitroisophthalate;

heterocyclic substances, such as 2-heptadecyl-2-imidazoline acetate, 2,4-dichloro-6-(o-chloroanilino)-s-triazine, O,O-diethyl phthalimidophosphonothioate, 5-amino-1-[bis(dimethylamino)phosphinyl]-3-phenyl-1,2,4-triazole, 2,3-dicyano-1,4-dithioanthraquinone, 2-thio-1,3-dithiolo[4,5-b]quinoxaline, methyl 1-(butylcarbamoyl)-2-benzimidazolecarbamate, 2-methoxycarbonylaminobenzimidazole, 2-(2-furyl) benzimidazole, 2-(4-thiazolyl)benzimidazole, N-(1,1,2,2-tetrachloroethylthio)tetrahydrophthalimide, N-trichloromethylthiotetrahydrophthalimide, N-trichloromethylthiophthalimide, N-dichlorofluoromethylthio-N',N'-dimethyl-N-phenylsulfodiamide, 5-ethoxy-3-trichloromethyl-1,2,3-thiadiazole, 2-thiocyanatomethyl-thiobenzothiazole, 1,4-dichloro-2,5-dimethoxybenzene, 4-(2-chlorophenylhydrazono)-3-methyl-5-isoxazolone, pyridine-2-thione 1-oxide, 8-hydroxyquinoline or its copper salt, 2,3-dihydro-5-carboxanilido-6-methyl-1,4-oxathiine, 2,3-dihydro-5-carboxanilido-6-methyl-1,4-oxathiine 4,4-dioxide, 2-methyl-5,6-dihydro-4H-pyran-3-carboxanilide, 2-methylfuran-3-carboxanilide, 2,5-dimethylfuran-3-carboxanilide, 2,4,5-trimethylfuran-3-carboxanilide, N-cyclohexyl-2,5-dimethylfuran-3-carboxamide, N-cyclohexyl-N-methoxy-2,5-dimethylfuran-3-carboxamide, 2-methylbenzanilide, 2-iodobenzanilide, N-formyl-N-morpholine-2,2,2-trichloroethyl acetal, piperazine-1,4-diylbis-1-(2,2,2-trichloroethyl)formamide, 1-(3,4-dichloroanilino)-1-formylamino-2,2,2-trichloroethane;

2,6-dimethyl-N-tridecylmorpholine or its salts, 2,6-dimethyl-N-cyclododecylmorpholine or its salts, N-[3-(p-tert-butylphenyl)-2-methylpropyl]-cis-2,6-dimethylmorpholine, N-[3-(p-tert-butylphenyl)-2-methylpropyl]piperidine, 1-[2-(2,4-dichlorophenyl)-4-ethyl-1,3-dioxolan-2-ylethyl]-1H-1,2,4-triazole, 1-[2-(2,4-dichlorophenyl)-4-n-propyl-1,3-dioxolan-2-yl-ethyl]-1H-1,2,4-triazole, N-(n-propyl)-N-(2,4,6-trichlorophenoxyethyl)-N'-imidazolylurea, 1-(4-chlorophenoxy)-3,3-dimethyl-1-(1H-1,2,4-triazol-1-yl)-2-butanone, (2-chlorophenyl)-(4-chlorophenyl)-5-pyrimidine-methanol, 5-butyl-2-dimethylamino-4-hydroxy-6-methylpyrimidine, bis(p-chlorophenyl)-3-pyridinemethanol, 1,2-bis(3-ethoxycarbonyl-2-thioureido)benzene, 1,2-bis(3-methoxycarbonyl-2-thio-ureido)benzene, [2-(4-chlorophenyl)ethyl]-(1,1-dimethylethyl)-1H-1,2,4-triazol-1-ethanol, 1-[3-(2-chlorophenyl)-1-(4-fluoro-phenyl)oxiran-2-ylmethyl]-1H-1,2,4-triazole, and a variety of fungicides, such as dodecylguanidine acetate, 3-[3-(3,5-dimethyl-2-oxycyclohexyl)-2-hydroxyethyl] glutarimide, hexachlorobenzene, methyl N-(2,6-dimethylphenyl)-N-(2-furoyl)-DL-alaninate, DL-N-(2,6-dimethylphenyl)-N-(2'-methoxyacetyl)alanine methyl ester, N-(2,6-dimethylphenyl)-N-chloroacetyl-D,L-2-amino-butyrolactone, DL-N-(2,6-dimethylphenyl)-N-(phenylacetyl)alanine methyl ester, 5-methyl-5-vinyl-3-(3,5-dichlorophenyl)-2,4-dioxo-1,3-oxazolidine, 3-(3,5-dichlorophenyl)-5-methyl-5-methoxymethyl-1,3-oxazolidine-2,4-dione, 3-(3,5-dichlorophenyl)-1-isopropyl-carbamoylhydantoin, N-(3,5-dichlorophenyl)-1,2-dimethylcyclopropane-1,2-dicarboximide, 2-cyano-[N-(ethylamino-carbonyl)-2-methoximino]acetamide, 1-[2-(2,4-dichlorophenyl)-pentyl]-1H-1,2,4-triazole, 2,4-difluoro-a-(1H-1,2,4-triazolyl-1-methyl)benzhydryl alcohol, N-(3-chloro-2,6-dinitro-4-trifluoromethylphenyl)-5-trifluoromethyl-3-chloro-2-amino-pyridine, 1-((bis(4-fluorophenyl) methylsilyl)methyl)-1H-1,2,4-triazole, strobilurins such as methyl E-methoximino-[α-(o-tolyloxy)-o-tolyl]acetate, methyl E-2-{2-[6-(2-cyanophenoxy)pyridimin-4-yloxy]phenyl}-3-methoxyacrylate, N-methyl-E-methoximino-[α-(2,5-dimethyloxy)-o-tolyl]acetamide.

Anilinopyrimidines such as N-(4,6-dimethylpyrimidin-2-yl)aniline, N-[4-methyl-6-(1-propynyl)pyrimidin-2-yl] aniline, N-(4-methyl-6-cyclopropylpyrimidin-2-yl)aniline.

Phenylpyrroles such as 4-(2,2-difluoro-1,3-benzodioxol-4-yl)pyrrole-3-carbonitrile.

Cinnamamides such as 3-(4-chlorophenyl)-3-(3,4-dimethoxy-phenyl)acryloylmorpholine.

EXAMPLE 1 a) 6-Fluoro-2-hydroxybenzonitrile 7.8 g of 2-methoxy-6-fluorobenzonitrile and 18.0 g of pyridine hydrochloride were heated for 5 hours at 195° C. under dry nitrogen. After cooling, the batch was partitioned between 50 ml of water and 50 ml of tert-butyl methyl ether, and the organic phase was subsequently extracted with 40 ml of 2N NaOH. The alkali extract was brought to pH 5 and subsequently extracted twice with in each case 40 ml of tert-butyl methyl ether. After the solvent had been evaporated, 4.7 g of the desired product were obtained as an oil (HPLC: 93%).

NMR(DMSO) ppm: 6.8–6.95 m(2H); 7.5–7.6 m(1H); 11.8 s,br(1H).

b) 2-Difluoromethoxy-6-fluorobenzonitrile 6.3 g of chlorodifluoromethane were passed into a stirred mixture of 10.0 g of 2-hydroxy-6-fluorobenzonitrile, 50 ml of 1,2-dimethoxyethane and 25 ml of NaOH (33%) at 75° C. (the reflux condenser was cooled with dry ice), and stirring was continued for one hour at 70–75° C. After cooling, the batch was diluted with 300 ml of water and extracted three times using in each case 150 ml of tert-butyl methyl ether. After the solvent had been vaporated, 6.5 9 of the desired product were obtained as an oil.

NMR (CDCl$_3$) ppm: 6.7 t(1H); 7.05–7.20 m(2H); 7.55–7.70 m(1H).

c) 2-Difluoromethoxy-6-fluorobenzamidoxime

A mixture of 6.4 g of 2-difluoromethoxy-6-fluorobenzonitrile and 3.1 g of hydroxylamine hydrochloride, 2.6 g of sodium carbonate, 7 ml of water and 35 ml of ethanol was stirred for 20 hours at 75° C.

After the solvent had been evaporated, the residue was partitioned between 40 ml of 2N HCl and 20 ml of ethyl acetate. After the HCl phase had been separated off, rendered neutral to pH 7 and extracted three times with in each case 40 ml of tert-butyl methyl ether, the solvent was evaporated. This gave 6.0 g of the desired product.

NMR(DMSO) ppm: 5.9 s(2H); 7.0–7.2 m(2H); 7.15 t(1H), 7.4–7.44 m(1H); 9.5 s(1H).

d) 2-Difluoromethoxy-6-fluorobenzamide O-cyclopropylmethyl oxime 0.4 g of 80% pure sodium hydride was added to a solution of 3.0 g of 2-difluoromethoxy-6-fluorobenzamidoxime in 30 ml of dimethylformamide (DMF) at 0 to 5° C. and the mixture was stirred at this temperature for 3 hours. 1.8 g of bromocyclopropylmethane were subsequently added at the same temperature, and stirring was subsequently continued for 2 hours at 5° C. and overnight at room temperature. The batch was stirred into 300 ml of water and extracted three times with in each case 70 ml of cyclohexane. After the cyclohexane had been evaporated, 1.9 g of the desired product were obtained.

NMR(CDCl$_3$) ppm: 0.3 m(2H); 0.55 m(2H); 1.2 m(1H); 3.9 d(2H); 4.85 s,br(2H); 6.6 t(1H); 6.85–7.1 m(2H); 7.35–7.45 m(1H).

e) N-Phenylacetyl-2-difluoromethoxy-6-fluorobenzamide O-cyclopropylmethyl oxime (Compound I.6 of Table 1).

1.9 g of 2-difluoromethoxy-6-fluorobenzamide O-cyclopropylmethyl oxime, which had been obtained in step d), and 1.5 g of phenylacetyl chloride were refluxed for 20 hours together with 40 ml of toluene. After cooling, 40 ml of water were added, and the pH was brought to 11. After the solvent had been evaporated and the residue subsequently subjected to column chromatography on silica gel with a 99:1 mixture of cyclohexane and ethyl acetate as the eluent, 1.6 g of the desired product of m.p. 58–60° C. were isolated from the toluene phase.

NMR(CDCl$_3$) ppm: 0.2 m(2H); 0.50 m(2H); 1.0 m(1H); 3.9 d(2H); 6.4 t(1H); 6.85–7.0 m(2H); 7.2–7.5 m(6H); 8.5 s(1H).

N-Phenylacetyl-2-difluoromethoxy-6-fluorobenzamide O-allylmethyl oxime (Compound I.3. of Table 1) was obtained in a similar manner as an oil.

EXAMPLE 2

Preparation of 2-hydroxy-5,6-difluorobenzonitrile a) Preparation of 2-methoxy-5,6-difluorobenzaldehyde oxime At 20–25° C., a solution of 29.4 g of 2-methoxy-5,6-difluoro-benzaldehyde (according to Ex. 27 of WO 97/03071) was added dropwise with stirring to a mixture of 16.0 g of hydroxylamine hydrochloride, 18.9 g of sodium acetate and 110 ml of 90% strength aqueous methanol. The mixture was stirred for 16 hours, the methanol was evaporated, the mixture was made into a paste using 250 ml of water and then washed and dried, giving 28.3 g of the desired product of m.p. 199–201° C.

b) Preparation of 2-methoxy-5,6-difluorobenzonitrile 20 drops of dimethylformamide and 16.6 g of thionyl chloride were added to a suspension of 18.7 g of the product obtained according to a) in 100 ml of toluene, and care was taken that the temperature did not rise higher than 30° C. After 4 hours of stirring at 30° C., toluene and thionyl chloride were evaporated under reduced pressure and 16.5 g of the desired product were isolated as an oil. NMR (CDCl$_3$) ppm: 3.9s(3H); 6.65–6.75m(1H); 7.3–7.45m(1H).

c) Preparation of 2-hydroxy-5,6-difluorobenzonitrile

At 50° C., 21.7 g of AlCl$_3$ were added a little at a time with stirring to a solution of 23.0 g of the product obtained according to b) in 70 ml of toluene. After the addition, the mixture was heated at reflux for 2 hours. After cooling, the reaction mixture was poured into 350 ml of water and adjusted to pH 1 using 2N HCl. The resulting crude product was extracted with tert-butyl methyl ether (2×100 ml) and purified by dissolving in 2N NaOH (2×80 ml) and acidification of the alkaline phase to pH 5 using 2N HCl. After extraction with tert-butyl methyl ether (2×80 ml), drying and evaporation of the solvent, 19.9 g of the desired product were isolated as an oil. NMR (CDCl$_3$) ppm: 6.45 s,brd(1H); 6.7–6.8 m(1H); 7.25–7.4 m(1H).

EXAMPLE 3

Efficacy Against Powdery Mildew of Wheat

Leaves of wheat seedlings cv. "Frühgold" grown in pots were sprayed to runoff point with aqueous preparation of active ingredient made with a stock solution composed of 10% active ingredient, 63% cyclohexanone and 27% emulsifier and, 24 hours after the spray coating had dried on, dusted with spores of powdery mildew of wheat (*Erysiphe graminis* f.sp.tritici). The test plants were subsequently placed in the greenhouse at from 20 to 22° C. and a relative atmospheric humidity of 75 to 80%. After 7 days, the extent of the mildew development was determined visually in % of the total leaf area.

The plants which had been treated with an aqueous preparation comprising 63 ppm of the active ingredients I.3, I.6, I.8, I.9, I.10, I.12, I.13 and I.29 of Table 1 were free from disease while the disease level of the untreated plants was 80%.

EXAMPLE 4

Efficacy Against Powdery Mildew of Wheat

Leaves of wheat seedlings cv. "Frühgold" grown in pots were sprayed to runoff point with aqueous preparation of active ingredient made with a stock solution composed of 10% active ingredient, 63% cyclohexanone and 27% emulsifier and, 24 hours after the spray coating had dried on, dusted with spores of powdery mildew of wheat (*Erysiphe graminis* f.sp.tritici). The test plants were subsequently placed in the greenhouse at from 20 to 22° C. and a relative atmospheric humidity of 75 to 80%. After 7 days, the extent of the mildew development was determined visually in % of the total leaf area.

The plants which had been treated with the active ingredients II.1 and II.3 of Table 2 were free from disease while the disease level of the untreated plants was 80%.

We claim:

1. A benzamidoxime of formula V

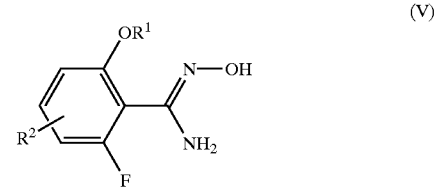

(V)

wherein

R$^1$ is difluoromethyl, and

R$^2$ is hydrogen or fluorine.

2. The benzamidoxime of formula V defined in claim 1, where R$^2$ is fluorine and is at the 5-position of the phenyl ring.

3. A benzamidoxime of formula VI

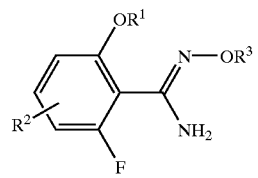
(VI)

wherein
R$^1$ is difluoromethyl,
R$^2$ is hydrogen or fluorine, and
R$^3$ is C$_1$–C$_4$-alkyl which may be substituted by cyano, C$_1$–C$_4$-haloalkyl, C$_1$–C$_4$-alkoxy-C$_1$–C$_4$-alkyl, C$_3$–C$_6$-alkenyl, C$_3$–C$_6$-haloalkenyl, C$_3$–C$_6$-alkynyl or C$_3$–C$_8$-cycloalkyl-C$_1$–C$_4$-alkyl.

4. The benzamidoxime of formula VI defined in claim 3, where R$^2$ is fluorine and is at the 5-position of the phenyl ring.

* * * * *

UNITED STATES PATENT AND TRADEMARK OFFICE
CERTIFICATE OF CORRECTION

PATENT NO.    : 6,509,501 B2
DATED         : January 21, 2003
INVENTOR(S)   : Eicken et al.

It is certified that error appears in the above-identified patent and that said Letters Patent is hereby corrected as shown below:

<u>Title page,</u>
Item [62], Related U.S. Application Data, "now Pat. No. 6,417,398" should be -- now Pat. No. 6,420,605 --.

Signed and Sealed this

Twenty-fourth Day of June, 2003

JAMES E. ROGAN
*Director of the United States Patent and Trademark Office*